United States Patent [19]

Wolvek

[11] Patent Number: 4,540,404
[45] Date of Patent: Sep. 10, 1985

[54] BALLOON CATHETER WITH INTRINSIC INTRODUCER FOR PERCUTANEOUS INSERTION INTO A BLOOD VESSEL OVER A GUIDE WIRE, AND METHOD OF USE

[75] Inventor: Sidney Wolvek, Brooklyn, N.Y.

[73] Assignee: Datascope Corp., Oakland, N.J.

[21] Appl. No.: 459,117

[22] Filed: Jan. 19, 1983

[51] Int. Cl.³ ............................................. A61M 25/00
[52] U.S. Cl. ..................................... 604/96; 604/164;
128/1 D
[58] Field of Search ...................... 128/1 D, 1 R, 344;
604/96, 164, 174

[56] References Cited

U.S. PATENT DOCUMENTS 3,985,601 10/1976 Panagrossi ........................... 604/103
4,413,989 11/1983 Schjeldahl .............................. 604/96
4,416,267 11/1983 Garren et al. ....................... 128/1 R Primary Examiner—Stephen C. Pellegrino
Attorney, Agent, or Firm—Darby & Darby

[57] ABSTRACT

A balloon catheter comprises a tip having a tapered distal end, a central lumen, and a balloon membrane coaxial with and surrounding the central lumen and connected to the tip. A sheath is slidable over the balloon to form an assembly, and a guide wire is slidable through the central lumen and insertable into a blood vessel for guiding the tip, membrane and sheath to a location within the blood vessel selected for therapy. The sheath fits loosely over the balloon, whereby the sheath can be withdrawn to expose the balloon at the selected location and the balloon can then be inflated to provide therapy.

7 Claims, 6 Drawing Figures

BALLOON CATHETER WITH INTRINSIC INTRODUCER FOR PERCUTANEOUS INSERTION INTO A BLOOD VESSEL OVER A GUIDE WIRE, AND METHOD OF USE

BACKGROUND OF THE INVENTION

1. Field of Invention

This invention relates to inflatable balloon catheters for percutaneous introduction into the human body and, more particularly, to novel and highly effective inflatable balloon catheters that are designed to be inserted over a guide wire.

2. Description of State of the Art

Certain vascular diseases can be treated by inserting a balloon, called an intra-aortic balloon (or IAB) within the appropriate blood vessel and advancing it to an appropriate position in the vasculature. The balloon is then inflated and deflated sequentially as determined by the disease. Dual-lumen balloon catheters designed to be inserted percutaneously over a guide wire into a blood vessel, without vascular surgical procedures, are becoming the method of choice for providing this form of therapy.

The present method of percutaneous balloon catheter insertion requires first the placement of a guide wire within the blood vessel of the patient, followed by the placement of an introducer sheath/dilator over the guide wire into the blood vessel of the patient. After the sheath/dilator has been advanced into the blood vessel, the physician prepares the IAB for insertion by wrapping it outside the body. The dilator and safety guide portions are removed from the body, allowing only the sheath portion of the introducer to communicate with the interior of the blood vessel.

The wrapping means is removed from the balloon and a second guide wire inserted into the balloon from its catheter end fitting and advanced through the central lumen of the balloon until it exits through the opening of the balloon tip into the sheath. The second guide wire is then advanced an appropriate distance into the blood vessel. The balloon is now advanced along the guide wire until it reaches the location within the blood vessel that is appropriate for the therapy. Visualization of the position of the balloon is achieved, for example, by fluoroscopy using the guide wire or a radio opaque portion of the balloon. The guide wire is then removed and therapy is commenced. The central lumen through which the guide wire had passed is now available for blood pressure monitoring or other monitoring or therapeutic uses.

Although the foregoing procedure is a safe, rapid and efficacious way of intra-aortic balloon insertion, the prerequisite insertion of the introducer sheath/dilator is a step which requires time and equipment to perform, often under circumstances such that time is a critical factor to patient survival, as during cardiogenic shock.

The construction of state of the art introducer sheath/dilators permits the leading edge of the sheath to slip over the tapered portion of the dilator during insertion into the body tissues. This permits distortion of the leading edge of the introducer sheath. Tearing of the blood vessel may result as it is entered by the distorted portion of the sheath. Further, the balloon must be wrapped for insertion into the sheath. This is an operation which demands time and a certain degree of skill.

During the foregoing described procedure, arterial bleeding through the sheath must be carefully controlled during the time interval between the removal of the guide wire and dilator from the sheath and the insertion of the wrapped balloon. Often, especially in a hypovolemic patient, this loss of blood may be critical. Also, when the balloon is wrapped, spiral interstices are produced along its length. The interstices of the wrapped balloon membrane do not provide for the complete occlusion of the sheath. Therefore, a certain amount of arterial bleeding takes place during the time that is required to fully insert the wrapped balloon membrane portion of the balloon catheter into the blood vessel.

In some cases, the sheath may have to be withdrawn partly from the percutaneous wound to permit complete introduction of the balloon membrane into the sheath, especially in those cases of extreme vascular tortuosity. This creates an additional loss of critical time and of critical blood.

The wrapped balloon must be advanced entirely through the restrictive confines of the sheath and then through a portion of the abdominal aorta in order to reach its proper position in the patient's thoracic aorta. The physician must judge whether the resistance felt is merely the result of passage through the sheath or is actually caused by the balloon's having entered a false lumen or aneurysm of the aorta after it has emerged from the sheath.

In the present state of the art, the balloon is required to be advanced beyond the confines of the sheath after some portion of its passage into the aorta. In the case of an extremely tortuous or diseased arterial system, the balloon may have to leave the sheath almost immediately upon entering the arterial system to be guided only by the guide wire. During this unprotected passage through the diseased arterial system it is liable to injury or puncture by sharp calcific plaque extending from the blood vessel walls.

SUMMARY OF THE INVENTION

An object of the invention is to provide a balloon catheter which may be inserted directly into a blood vessel over a single guide wire, without the need first to insert an introducer sheath/dilator, and without the need to exchange guide wires.

Another object of the invention is to provide an intra-aortic balloon which does not have to be wrapped or prepared in any other way by the physician prior to its insertion into the human body.

Another object is to provide a balloon catheter which will serve as its own introducer sheath/dilator.

A further object is to provide a balloon catheter which is integral with an introducer sheath in which the leading edge of the sheath cannot be damaged during insertion by the resistance of the tissue of the human body and cannot slip over the tapered portion of the dilator.

Other objects of the invention are to provide a balloon catheter which has a balloon membrane disposed within a sheath, which permits deployment of the balloon membrane from the sheath after insertion into the human body; and which can be inserted completely into the pumping position within the human body while remaining within its sheath, thereby protecting it from damage by sharp arterial plaque and obviating the resistance of the wrapped balloon to passage into and beyond the sheath.

The foregoing and other objects are attained in accordance with the invention by providing a balloon catheter whose tip which is first inserted into the vessel has a tapered distal end, a central lumen extending longitudinally of the catheter, and a balloon membrane coaxial with and surrounding the central lumen and connected to the tip.

A sheath is slidable over the balloon catheter to form an assembled unit of the balloon and sheath. A guide wire is slidable through the central lumen and insertable into a blood vessel for guiding the unit, i.e. balloon, membrane and sheath, to a location within the blood vessel selected for therapy. The sheath fits loosely over the balloon, whereby the sheath can be withdrawn to expose the balloon at the selected location and the balloon can be inflated to provide therapy.

BRIEF DESCRIPTION OF THE DRAWINGS

A better understanding of the invention may be gained from the following detailed description of the preferred embodiments thereof, in conjunction with the appended drawing, wherein.

DESCRIPTION OF THE PREFERRED EMBODIMENTS

Figure 1:
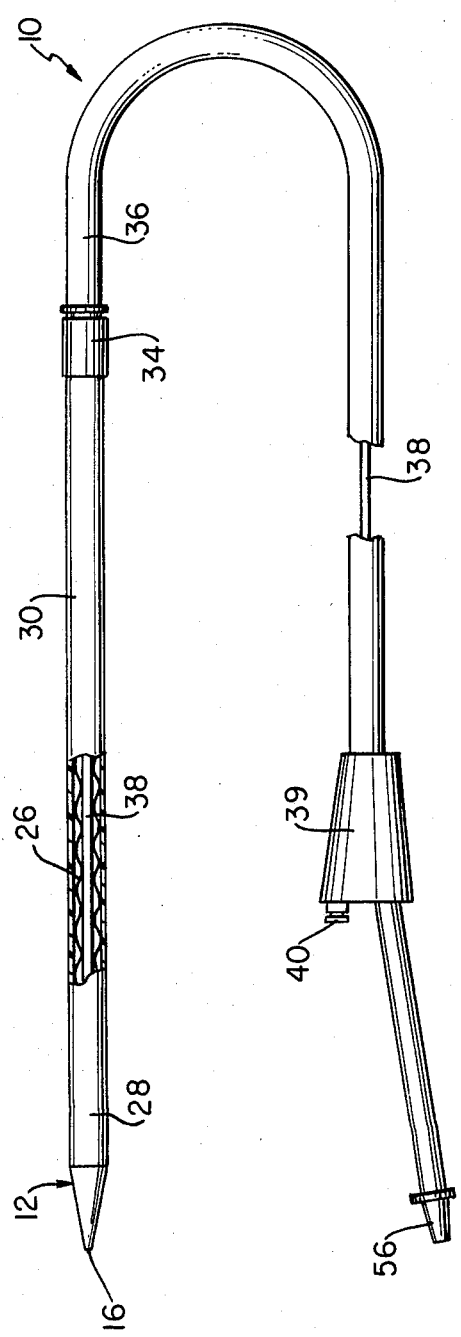
FIG. 1 is a view in elevation, partly broken away, of a device constructed in accordance with the invention.

FIG. 1 shows an overall view of the IAB 10 constructed in accordance with the invention. It comprises a tip 12 which has a through passage 14 (FIG. 2) forming an exit 16 at its distal end 18, which is defined as the end farthest from the practitioner and closest to the patient.

Figure 2A:
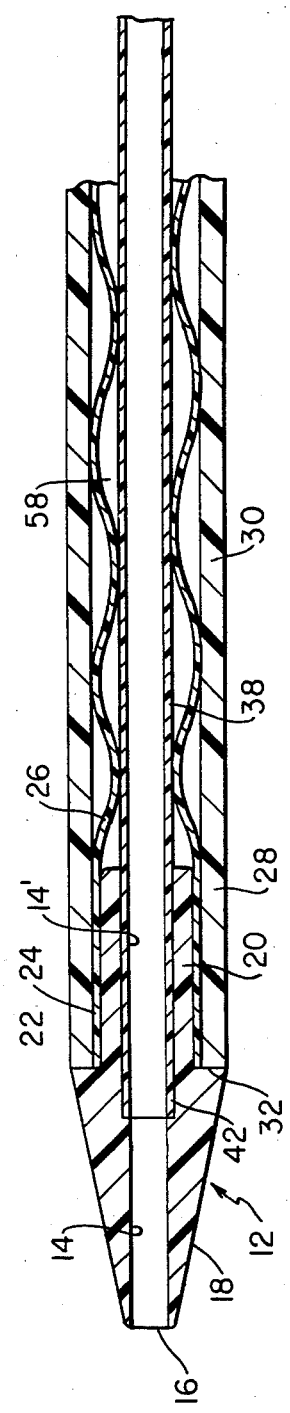
FIG. 2A is a view in axial section, on a scale enlarged with respect to FIG. 1, of the distal end of the device of FIG. 1.
Figure 2B:
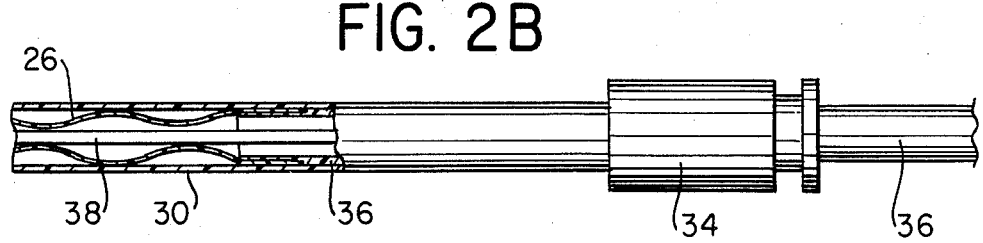
FIG. 2B is a view partly in axial section of an intermediate portion of the device of FIG. 1.

As FIGS. 2A and 2B together show, the balloon membrane 26 is securely attached at its proximal end to the distal end of a catheter 36 and at its distal end to the proximal end of the tip 12. A central lumen 38 is attached at its distal end to the tip 12 and passes through the catheter 36 with a clearance. In this manner, as described below, a fluid such as air can be pumped and evacuated through the catheter 36 and into the space 58 between the central lumen 38 and the balloon membrane 26 to inflate and deflate the balloon membrane 26 within the human vasculature.

The distal end 18 of the tip 12 is frusto-conical, angulated, or otherwise tapered to facilitate passage through the skin, subcutaneous tissue and arterial wall. The opposite or proximal end 20 of the tip 12 is considerably narrower than the base 22 of the tapered distal end 18 of the tip 12. The narrow proximal end 20 of the tip 12 is cylindrical, and the distal end 24 of a balloon membrane 26 is affixed thereto. The cylindrical portion 20 of the tip 12 also accommodates the distal end 28 of an introducer sheath 30. The sheath 30 is sufficiently rigid to prevent the longitudinal collapse of the balloon membrane 26 as the IAB 10 is inserted into the body and advanced along the artery.

The dimensions of the cylindrical proximal end 20 of the tip 12 and the thickness of the balloom membrane 26 allow a sliding fit of the distal end 28 of the sheath 30 thereover. The leading edge 32 of the sheath 30 abuts the base 22 of the tapered distal end 18 of the tip 12, thereby preventing the sheath 30 from overriding the distal end 18 of the tip 12.

The base 22 constitutes a shoulder facing in the proximal direction, since the outer dimension of the proximal end 20 of the tip 12 is less than the maximum outer dimension of the distal end 18 of the tip 12. The shoulder is radial with respect to the central lumen of the catheter and has an outer dimension at least as great as that of the sheath. This prevents the sheath 30 from overriding the distal end 18 of the tip 12 when pushed thereagainst and preserves the distal portion 28 and leading edge 32 of the sheath 30 from damage and undue distortion during insertion into the patient's tissue. Moreover, it preserves the tissue of the patient against undue trauma.

The balloon membrane 26 is contained within the sheath 30, the distal portion 28 of the sheath 30 abutting the base 22 of the frusto-conical portion 18 of the tip 12 as heretofore described, and the proximal or hub end 34 (FIG. 1) of the sheath 30 slidably enclosing the catheter portion 36 of the IAB 10, thereby fully enclosing the balloon membrane 26 for insertion into the human body.

The central lumen 38 within the balloon membrane 26 passes longitudinally through the catheter 36, its proximal end communicating with the exterior by means of a suitable fitting 39, 40 and the distal end 42 (FIG. 2A) communicating with the opening 14, 16 in the distal end 18 of balloon tip 12.

Figure 3:
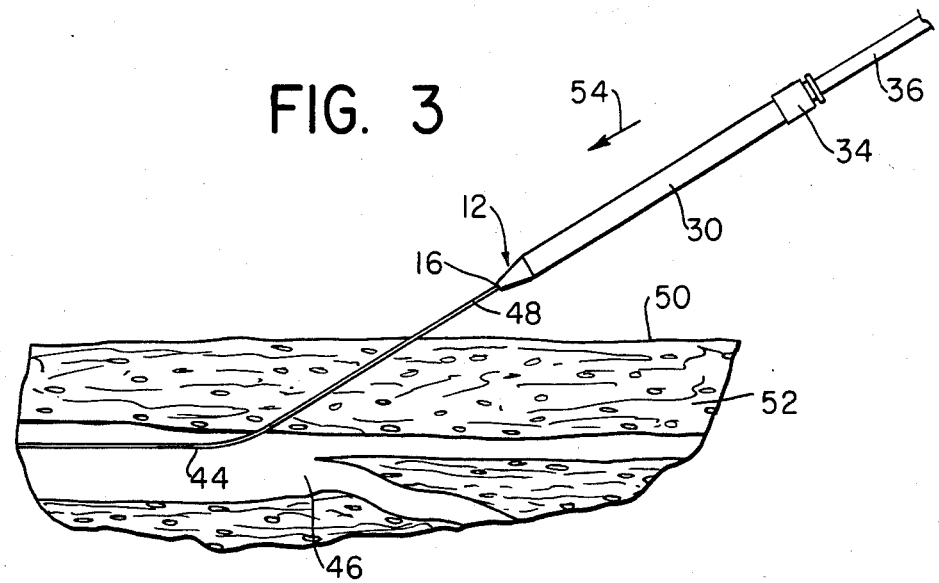
FIG. 3 is a view partly in elevation and partly in section showing one step in the use of a device according to the invention.

As FIG. 3 shows, a small diameter guide wire 44, typically 0.035" to 0.038" (about 0.089 cm to 0.097 cm) in diameter, has been placed within the blood vessel 46 of the patient. The proximal end 48 of guide wire 44 protrudes beyond the patient's skin line 50 and subcutaneous tissue 52. The opening 16 is placed over the protruding proximal end 48 of the guide wire 44, and the entire balloon catheter, the balloon membrane 26 being enclosed in the sheath 30 as shown in FIGS. 1 and 2, is advanced over the guide wire 44 in the direction shown by the arrow 54 to the skin line 50.

Figure 4:
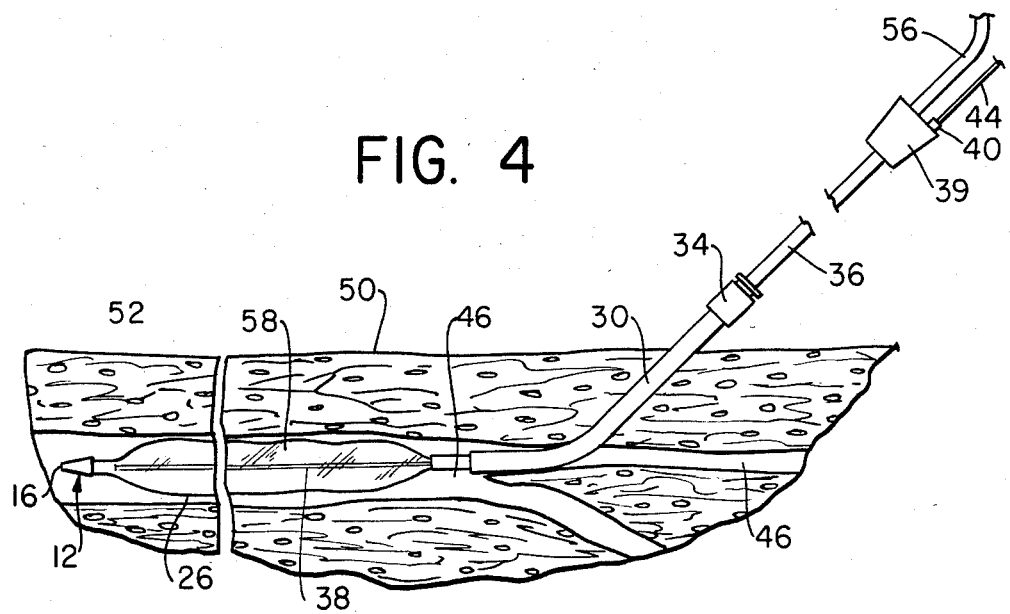
FIG. 4 is a view similar to FIG. 3 showing a later step in the use of a device according to the invention.

The sheath-enclosed balloon membrane 26 is advanced through the skin and tissue 52 of the patient, the frusto-conical distal end 18 dilating the tissue and facilitating the insertion. The device is advanced within the blood vessel 46 until it reaches the appropriate position for therapy within that blood vessel. This is often deep within the body and not as close to the point of entry as appears in FIG. 4. The sheath 30 is then withdrawn along catheter 36 until the balloon membrane 26 is completely uncovered, thereby permitting it to be deployed within the blood vessel as shown in FIG. 4.

At this point, the guide wire 44 may be removed and luer fitting 56 connected to a pump console (not shown) to provide the appropriate therapy to the patient. Specifically, by means of the pump console, a fluid such as air is introduced into the space 58 between the balloon membrane 26 and the central lumen 38 for the purpose of the balloon inflation. The central lumen 38 communicating to luer fitting 40 may now be used for blood pressure monitoring or other monitoring or therapeutic purposes.

The bore 14 of the tip 12 is formed with a counterbore 14' (FIG. 2A) at the proximal end thereof. The central lumen 38 fits tightly within the counterbore 14', whereby the bore 14 and central lumen 38 cooperate to form a smooth-walled, continuous passageway for the guide wire 44.

The central lumen 38 is rigid enough to support the assembly comprising the tip 12, balloon membrane 26 and central lumen 38 in place in the blood vessel 46 while the sheath 30 is withdrawn.

In use, therapy is provided within a blood vessel by the method of forming an assembly comprising (a) the tip 12 having a tapered distal end 18, (b) the central lumen 38 extending longitudinally of the catheter, and (c) the balloon membrane 26 coaxial with and surrounding the central lumen 38 and catheter 36. The sheath 30 is slid over the balloon 26 to complete the assembly. A single guide wire, for example the guide wire 44, is inserted into a blood vessel such as the vessel 46, and the completed assembly comprising elements (a), (b) and (c) mentioned above plus the sheath 30 is slid over the guide wire 44 and into the blood vessel 46, the guide wire 44 extending through the central lumen 38.

The assembly is advanced along the guide wire 44 to a location within the blood vessel 46 selected for therapy, and the sheath 30 is withdrawn to expose the balloon membrane 26, which is then inflated to provide therapy.

Figure 5:
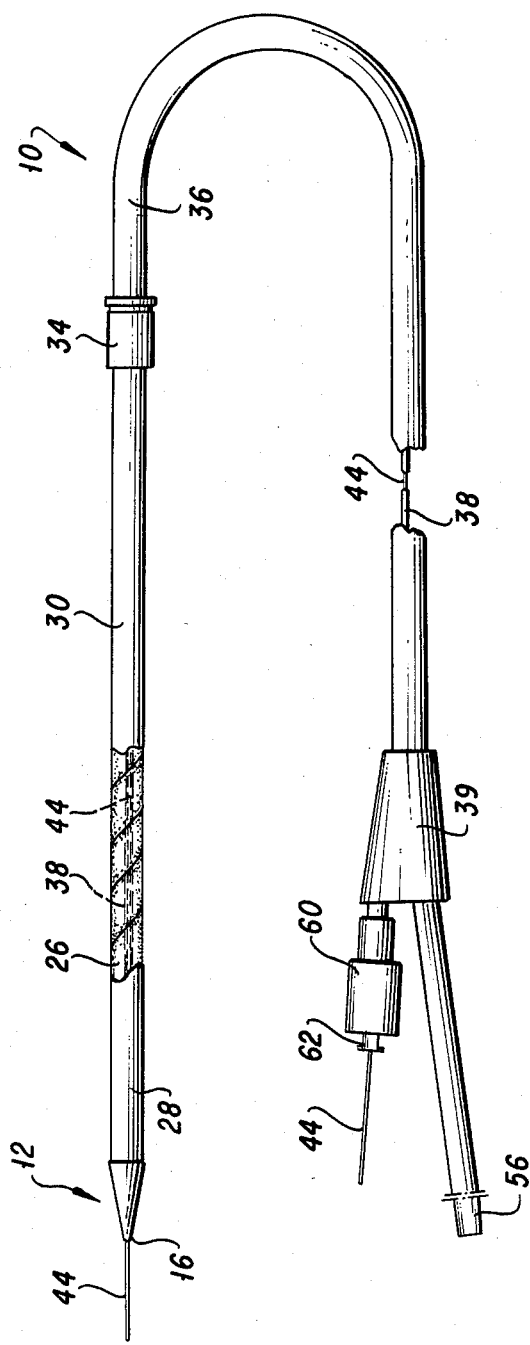
FIG. 5 is a view similar to FIG. 1 showing an alternative embodiment of the invention.

FIG. 5 shows an alternative embodiment of the invention in which the balloon membrane 26 has been prewrapped at the factory a specific number of turns prior to its insertion into the sheath 30 by means of wrapping knob 60.

Insertion into the patient is accomplished over the guide wire 44 as has been heretofore described. The balloon 26 is then advanced within the blood vessel until it reaches the appropriate position for therapy. The sheath 30 is then withdrawn along the catheter 36 until the balloon membrane 26 is completely uncovered. The balloon membrane 26 is then unwrapped by rotating the wrapping knob 60 attached to the proximal end of the central lumen 38. At this point the guide wire 44 may be removed from a luer fitting 62 which forms a portion of the wrapping knob 60. The central lumen 38 communicating with luer fitting 62 may now be used for blood pressure monitoring or other monitoring or therapeutic uses as has been heretofore described.

Although the wrapping knob 60 has been described as the means for unwrapping the prewrapped balloon membrane 26, it should be understood that other means may be used to achieve this unwrapping One such means, for instance, is described in copending U.S. patent application Ser. No. 202,868, in which the energy stored in the central lumen during wrapping is utilized to achieve unwrapping. It must therefore be understood that the present invention is not limited to any specific means of unwrapping the prewrapped balloon.

Thus there is provided in accordance with the invention a novel and highly effective inflatable balloon catheter that is designed to be inserted over a guide wire. A physician using the device of the invention need merely remove it from its sterile package (not shown) and insert it directly into the blood vessel over a single guide wire, without the need first to insert an introducer sheath/dilator and without the need to exchange guide wires. The leading edge of the sheath cannot be damaged during insertion and is not likely to damage patient tissue. The balloon membrane, as well, is protected by the sheath during insertion.

Many modifications of the preferred embodiments of the invention disclosed above will readily occur to those skilled in the art upon consideration of this disclosure. For example, the distal end 18 of the tip 12 need not be frusto-conical; it can be faceted, angulated, or otherwise configured so long as it is generally tapered in such a manner as to facilitate its entry into, and gradual enlargement of, a tissue entry wound with a minimum of trauma to the patient. Accordingly, the invention is to be construed as including all structures and methods which are respectively within the scope of the appended claims.

What is claimed is:

1. A balloon catheter comprising
a tip having a tapered distal end,
a central lumen extending longitudinally of said catheter,
a balloon membrane coaxial with and surrounding said central lumen and having its distal end connected to said tip,
a sheath slidable over said balloon to form an assembly,
a guide wire slidable through said central lumen and insertable into a blood vessel for guiding said tip, membrane and sheath to a location within said blood vessel selected for therapy,
said sheath fitting loosely over said balloon, whereby said sheath can be withdrawn along the balloon catheter to expose said balloon at said location and said balloon can then be inflated to provide therapy, and
wrapping means connected to said central lumen whereby said central lumen is rotatable about its axis to unwrap said balloon membrane after withdrawal of said sheath to facilitate deployment of said balloon at said location.

2. A balloon catheter according to claim 1 wherein
said tip is formed with a bore extending longitudinally thereof and with a counterbore at the proximal end of said bore,
said central lumen fitting tightly within said counterbore,
said bore and said central lumen cooperating to form a smooth-walled, continuous passageway for said guide wire.

3. A balloon catheter comprising:
a tip having a tapered distal end;
a central lumen extending longitudinally of said catheter;
a balloon membrane coaxial with and surrounding said central lumen and having its distal end connected to said tip;
a sheath slidable over said balloon to form an assembly;
a guide wire slidable through said central lumen and insertable into a blood vessel for guiding said tip, membrane and sheath to a location within said blood vessel selected for therapy;
said tip comprising a proximal end having an outer diameter reduced as compared to the maximum outer diameter of the distal end of said tip, thereby forming a shoulder facing the proximal direction;
said balloon membrane forming a tight connection with said proximal end;
said sheath being adapted to abut said shoulder, the outer dimension of said shoulder being at least as great as that of said sheath; and
said sheath fitting loosely over said balloon, whereby said sheath can be withdrawn to expose said balloon at said location and said balloon can then be inflated to provide therapy.

4. A balloon catheter according to claim 3 wherein said shoulder is radial with respect to said central lumen, therby minimizing the tendency of said sheath to override said shoulder when pushed thereagainst.

5. A method of providing therapy within a blood vessel by means including a balloon catheter comprising the steps of forming an assembly comprising (a) a tip having a tapered distal end, (b) a central lumen extending longitudinally of said catheter, and (c) a balloon membrane coaxial with and surrounding said central lumen and connected to said tip, sliding a sheath over said balloon to complete said assembly, inserting a single guide wire into said blood vessel, sliding said completed assembly over said guide wire and into said blood vessel, said guide wire extending through said central lumen, advancing said assembly along said guide wire to a location within said blood vessel selected for therapy, withdrawing said sheath to expose said balloon, and inflating said balloon.

6. A method according to claim 5 comprising the further step of prewrapping said balloon membrane with respect to said central lumen to facilitate sliding said sheath over said balloon.

7. A method according to claim 6 comprising the further step of unwrapping said balloon membrane after withdrawing said sheath to expose said balloon.

* * * * *